United States Patent
Feng et al.

(10) Patent No.: US 11,694,397 B2
(45) Date of Patent: Jul. 4, 2023

(54) METHOD FOR SETTING A LOCAL COORDINATE SYSTEM OF A TOOTH 3D DIGITAL MODEL

(71) Applicant: WUXI EA MEDICAL INSTRUMENTS TECHNOLOGIES LIMITED, Jiangsu (CN)

(72) Inventors: Yang Feng, Shanghai (CN); Xiaolin Liu, Shanghai (CN); Bowen Zhou, Shanghai (CN)

(73) Assignee: WUXI EA MEDICAL INSTRUMENTS TECHNOLOGIES LIMITED, Jiangsu (CN)

(*) Notice: Subject to any disclaimer, the term of this patent is extended or adjusted under 35 U.S.C. 154(b) by 103 days.

(21) Appl. No.: 16/967,671

(22) PCT Filed: Mar. 12, 2019

(86) PCT No.: PCT/CN2019/077805
§ 371 (c)(1),
(2) Date: Aug. 5, 2020

(87) PCT Pub. No.: WO2019/214339
PCT Pub. Date: Nov. 14, 2019

(65) Prior Publication Data
US 2021/0217233 A1    Jul. 15, 2021

(30) Foreign Application Priority Data
May 9, 2018  (CN) .......................... 201810445610.0

(51) Int. Cl.
*G06T 17/00*    (2006.01)
*A61C 7/00*    (2006.01)
(Continued)

(52) U.S. Cl.
CPC ............ *G06T 17/005* (2013.01); *A61C 7/002* (2013.01); *G06N 3/04* (2013.01); *G06N 3/08* (2013.01); *A61C 2007/004* (2013.01)

(58) Field of Classification Search
None
See application file for complete search history.

(56) References Cited

U.S. PATENT DOCUMENTS

2016/0019688 A1 * 1/2016 Li .......................... G06T 7/0004
                                                                382/110
2017/0154471 A1 * 6/2017 Woo ....................... G06T 19/006
(Continued)

FOREIGN PATENT DOCUMENTS

CN    105380723 A  *  3/2016   ......... A61C 13/0004
CN    105931291 A     9/2016
(Continued)

OTHER PUBLICATIONS

International Search Report and Written Opinion from International Patent Application No. PCT/CN2019/077805 dated May 29, 2019.

*Primary Examiner* — Aaron M Richer
(74) *Attorney, Agent, or Firm* — Greenberg Traurig, LLP

(57) ABSTRACT

In one aspect of the present application, a computer-implemented method for setting a local coordinate system of a tooth 3D digital model is provided, the method comprises: obtaining a first 3D digital model representing a first tooth, wherein the first 3D digital model is based on a world coordinate system; and setting a local coordinate system for the first 3D digital model using a first artificial neural network based on the first 3D digital model, where the first artificial neural network is a trained deep learning artificial neural network.

11 Claims, 5 Drawing Sheets

(51) Int. Cl.
*G06N 3/04* (2023.01)
*G06N 3/08* (2023.01)

(56) References Cited

U.S. PATENT DOCUMENTS

| | | | |
|---|---|---|---|
| 2017/0184630 A1* | 6/2017 | Chan | G06F 17/00 |
| 2018/0303581 A1* | 10/2018 | Martz | A61C 9/0006 |
| 2019/0244423 A1* | 8/2019 | Brettle | G06N 3/08 |
| 2019/0354772 A1* | 11/2019 | Tasli | G06T 7/33 |
| 2019/0362178 A1* | 11/2019 | Huang | G06V 10/42 |

FOREIGN PATENT DOCUMENTS

| | | | |
|---|---|---|---|
| CN | 107260335 A | 10/2017 | |
| CN | 107301673 A | 10/2017 | |
| CN | 107374758 A | 11/2017 | |
| WO | 2008/096017 A2 | 8/2008 | |

* cited by examiner

METHOD FOR SETTING A LOCAL COORDINATE SYSTEM OF A TOOTH 3D DIGITAL MODEL

RELATED APPLICATIONS

The present application is a national phase filing under 35 USC 371 of International Application No. PCT/CN2019/077805, filed on Mar. 12, 2019, which claims priority of Chinese Patent Application No. 201810445610.0, filed May 9, 2018, the entire contents and disclosures of which are hereby incorporated by reference.

FIELD OF THE APPLICATION

The present application generally relates to a method for setting a local coordinate system of a tooth 3D digital model.

BACKGROUND

With the continuous development of computer science, dental professionals increasingly rely on computer techniques to improve the efficiency of dental diagnosis and treatment.

A tooth 3D digital model is often used in computer-aided dental diagnosis and treatment. For ease of process and calculation, a world coordinate system may be established and a local coordinate system be established for each tooth. For each tooth, its position and pose may be represented by combination of the world coordinate system and the local coordinate system of the tooth. In some computer-aided dental diagnosis and treatment applications, for example, a computer-aided method for generating orthodontic treatment plan, how local coordinate systems are set is very crucial.

Currently, local coordinate systems are usually set manually. However, local coordinate systems such set have the following drawbacks: firstly, each technician might have different understanding of local coordinate systems, so it is difficult to ensure the consistency in the setting of local coordinate systems; secondly, a lot of time and labor is required to manually set a local coordinate system for each tooth, and additionally optimization of local coordinate systems is like performing another round manual setting, therefore, manual setting local coordinate systems consumes higher time and labor costs.

In view of the above, it is necessary to provide a new method of setting local coordinate systems.

SUMMARY

In one aspect, the present application provides a computer-implemented method for setting a local coordinate system for a tooth 3D digital model, comprising: obtaining a first 3D digital model representing a first tooth, wherein the first 3D digital model is based on a world coordinate system; and based on the first 3D digital model, setting a local coordinate system for it using a first artificial neural network, wherein the first artificial neural network is a trained deep learning artificial neural network.

In some embodiments, the first artificial neural network may be a multi-layer perceptron.

In some embodiments, the computer-implemented method for setting a local coordinate system of a tooth 3D digital model may further comprise: obtaining a first predicted vector using the first artificial neural network based on the first 3D digital model, wherein the first predicted vector corresponds to a first coordinate axis of the local coordinate system, the first coordinate axis is one of the y-axis and z-axis of the local coordinate system, and the other of the y-axis and z-axis of the local coordinate system is a second coordinate axis; determining the x-axis of the local coordinate system using a principal component analysis method based on the first 3D digital model; determining the second coordinate axis based on the determined x-axis and first predicted vector; and determining the first coordinate axis based on the determined x-axis and second coordinate axis.

In some embodiments, the principal component analysis method may be a Normals Principal Component Analysis method.

In some embodiments, the computer-implemented method for setting a local coordinate system of a tooth 3D digital model may further comprise: obtaining a second predicted vector using a second artificial neural network based on the first 3D digital model, wherein the second artificial neural network is a trained deep learning artificial neural network and is used to predict the x-axis of the local coordinate system, and the second predicted vector corresponds to the x-axis of the local coordinate system; generating three feature vectors using the principal component analysis method based on the first 3D digital model; and selecting from the three feature vectors the one having a minimum angle with respect to a straight line where the second predicted vector lies, giving the selected feature vector a correct sign according to the second predicted vector, and taking it as the x-axis of the local coordinate system.

In some embodiments, determining the second coordinate axis by calculating cross product of the determined x-axis and first predicted vector; and determining the first coordinate axis by calculating cross product of the determined x-axis and second coordinate axis.

In some embodiments, the first coordinate axis of the local coordinate system may be the z-axis.

In some embodiments, the computer-implemented method for setting a local coordinate system of a tooth 3D digital model may further comprise: simplifying the first 3D digital model such that the number of its vertices is equal to a predetermined number N, to obtain a first digital data set, and obtaining the first predicted vector using the first artificial neural network based on the first digital data set, wherein N is a natural number.

In some embodiments, the computer-implemented method for setting a local coordinate system of a tooth 3D digital model may further comprise: centralizing the simplified data set to obtain a second digital data set, obtaining the first predicted vector using the first artificial neural network based on the second digital data set, and determining the x-axis of the local coordinate system using the principal component analysis method based on the second digital data set.

In some embodiments, the computer-implemented method for setting a local coordinate system of a tooth 3D digital model may further comprise: normalizing the second digital data set to obtain a third digital data set, and obtaining the first predicted vector using the first artificial neural network based on the third digital data set.

In some embodiments, an output layer of the first artificial neural network may comprise an EuclideanLoss cost function for training parameters of various layers by back propagation.

In some embodiments, the computer-implemented method for setting a local coordinate system of a tooth 3D digital model may further comprise: selecting the first artificial neural network from a plurality of artificial neural networks according to the type of the first tooth, wherein the plurality of artificial neural networks are trained deep learning artificial neural networks for setting local coordinate systems for different types of teeth respectively.

In some embodiments, the first artificial neural network may be one of: a Multi-layer Perceptron, an Octree-Based Convolutional Neural Network, a Convolutional Neural Network, a Recurrent Neural Network, Reinforcement Learning and a Generative Adversarial Network.

In some embodiments, the first artificial neural network may be trained with a plurality of tooth 3D digital models each having a manually set local coordinate system, where each of the plurality of tooth 3D digital models represents a tooth which is the same type as the first tooth.

BRIEF DESCRIPTION OF THE DRAWINGS

The above and other features of the present application will be further illustrated below with reference to figures and their detailed description. It should be appreciated that these figures only show several exemplary embodiments according to the present application, so they should not be construed as limiting the protection scope of the present application. Unless otherwise specified, the figures are not necessarily drawn to scale, and similar reference numbers therein denote similar components.

DETAILED DESCRIPTION OF ILLUSTRATED EMBODIMENTS

In the following detailed description, reference is made to the accompanying drawings, which form a part thereof. Exemplary embodiments in the detailed description and figures are only intended for illustration purpose and not meant to be limiting. Inspired by the present application, those skilled in the art can understand that other embodiments may be utilized and other changes may be made, without departing from the spirit or scope of the present application. It will be readily understood that aspects of the present application described and illustrated herein can be arranged, replaced, combined, separated and designed in a wide variety of different configurations, all of which are explicitly contemplated and make part of the present application.

After a lot of work, the Inventors of the present application developed a computer-implemented method for setting a local coordinate system of a tooth 3D digital model based on deep learning. A trained deep learning artificial neural network is used to set the local coordinate system of the tooth 3D digital model.

Figure 1:
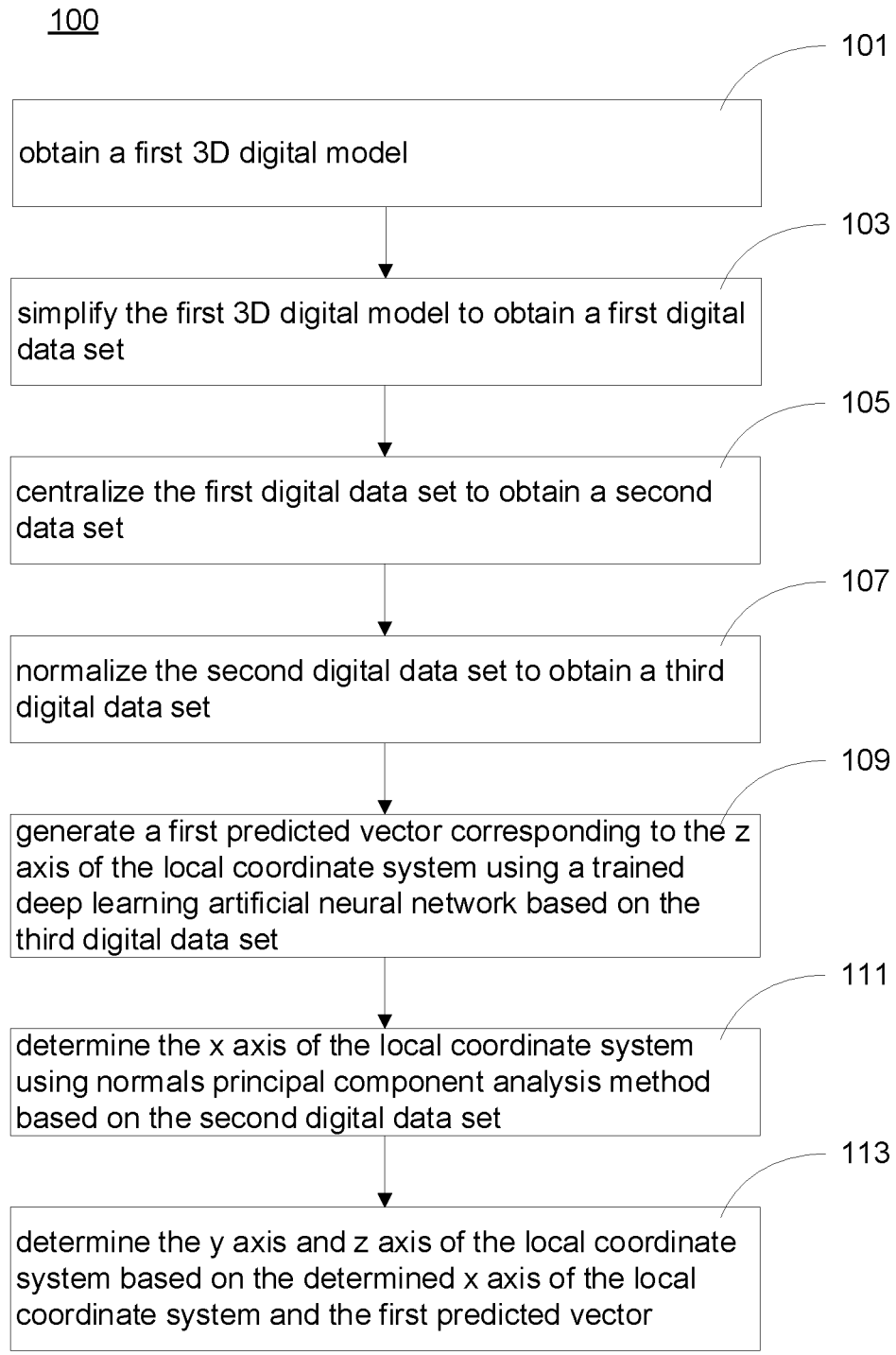
FIG. 1 schematically illustrates a flow chart of a computer-implemented method for setting a local coordinate system of a tooth 3D digital model according to an embodiment of the present application.

Referring to FIG. 1, it schematically illustrates a flow chart of a computer-implemented method 100 for setting a local coordinate system of a tooth 3D digital model according to one embodiment of the present application.

In one embodiment, the computer-implemented method 100 for setting a local coordinate system of a tooth 3D digital model is based on Multi-Layer Perceptron (abbreviated as MLP).

In one embodiment, to improve prediction accuracy of the artificial neural network, one artificial neural network may be established for each type of teeth, for example, one artificial neural network may be established for each of teeth No. 1 to No. 7, each of which is for setting local coordinate systems for a corresponding type of teeth.

In 101, a first 3D digital model is obtained.

The first 3D digital model is based on the world coordinate system and represents a first tooth, and coordinate values of its vertices are coordinate values in the world coordinate system.

In one embodiment, the world coordinate system may be manually set. For example, a vector perpendicular to an occlusal surface may be taken as the Z-axis of the world coordinate system, a line passes through cusps of two No. 6 teeth may be taken as the direction of X-axis, and the Y-axis may be determined based on these two coordinate axes.

There are many methods for obtaining a 3D digital model of a patient's teeth. In one embodiment, a 3D digital model representing a patient's dentition may be obtained by scanning the patient's jaw directly. In another embodiment, a 3D digital model representing the patient's dentition may be obtained by scanning a mockup model, e.g., a plaster model of the patient's jaw. In a further embodiment, a 3D digital model representing the patient's dentition may be obtained by scanning an impression of the patient's jaw. 3D digital models representing various teeth respectively may be obtained by segmenting a 3D digital model representing the patient's dentition.

In one embodiment, a 3D digital model of teeth may be established based on triangle mesh, and the below embodiments will use such 3D digital models for illustration purpose. It is understood that a 3D digital model of teeth may also be established based on other meshes, for example, quadrilateral mesh, pentagonal mesh, hexagonal mesh etc., which will not be described in detail.

In 103, the first 3D digital model is simplified to obtain a first digital data set.

The numbers of vertices/facets of unprocessed original tooth 3D digital models might be different, which is not good for the training of artificial neural networks and setting local coordinate systems using the trained artificial neural networks. Therefore, a 3D digital model may be simplified before being input to an artificial neural network, such that the number of vertices/facets thereof is equal to a predetermined value N. In one embodiment, the predetermined value may be set to 2048 or 1024, namely, the number of vertices of the simplified 3D digital model equals to 2048 or 1024. It is understood that the predetermined value may be set to other numbers according to specific situations and needs. Herein, the first digital data set represents the simplified 3D digital model.

In one embodiment, the first 3D digital model may be simplified using an edge contraction algorithm with Quadric Error Metrics as a cost.

First, a Q matrix may be calculated for each vertex of the first 3D digital model according to Equation (1):

$$Q = \Sigma_{p \in planes(v)} K_p \quad \text{Equation (1)}$$

where planes(v) represents a set of planes related to original vertices (vertices of the unsimplified first 3D digital model), and $K_p$ may be written as the following Equation (2), $$K_p = pp^T = \begin{bmatrix} a^2 & ab & ac & ad \\ ab & b^2 & bc & bd \\ ac & bc & c^2 & cd \\ ad & bd & cd & d^2 \end{bmatrix} \quad \text{Equation (2)}$$

where p may be written as the following Equation (3), $$p = [a\ b\ c\ d]^T \quad \text{Equation (3)}$$

where p stands for coefficients of the following plane equation (4), $$ax + by + cz + d = 0 \quad \text{Equation (4)}$$

where a, b and c satisfy the following condition:

$$a^2 + b^2 + c^2 = 1 \quad \text{Equation (5)}$$

In one embodiment, a merge cost may be calculated for each pair of adjacent vertices, then a set of vertex pairs with a minimum merge cost may be iteratively selected for contraction, and errors of all relevant edges may be updated. The simplified vertex set may be obtained based on the calculation of the Q matrix.

The number of vertices of the simplified 3D digital model may not equal to the predetermined value, in this case, vertices may be added or deleted so that the number of vertices of the first digital data set equals to the predetermined value.

Inspired by the present application, it is understood that besides edge contraction algorithm with Quadric Error Metrics as a cost, any other suitable algorithms may be used to simplify the first 3D digital model.

In 105, the first digital data set is centralized to obtain a second digital data set.

In one embodiment, a mean value of coordinates of the vertices of the first digital data set may be calculated, to obtain coordinates of a center point, and then the coordinates of the center point is subtracted from the coordinates of the vertices of the first digital data set to obtain the second digital data set.

In 107, the second digital data set is normalized to obtain a third digital data set.

In one embodiment, the second digital data set may be normalized in all dimensions respectively to obtain the third digital data set. For example, the normalization along the X-axis of the world coordinate system may be performed according to the following Equation (6):

$$m - \text{data}(X) = \frac{(\text{data}(X) - \min(\text{data}(X)))}{\max(\text{data}(X)) - \min(\text{data}(X))} \quad \text{Equation (6)}$$

wherein m-data(X) stands for data after the normalization along the X-axis of the world coordinate system; min(data(X)) stands for a minimum X coordinate value of the vertices; max(data(X)) stands for a maximum X coordinate value of the vertices.

In one embodiment, the data obtained by the normalization may be saved in hdf5 (Hierarchical Data Format version 5.0) format, i.e., the third digital data set is in hdf5 format.

In one embodiment, the Y-axis component and Z-axis component in the world coordinate system may be normalized using min(data(X)) and max(data(X)), namely, isotropic normalization may be performed, the performance of which is proven to be good by experiments, which will not be described in detail here. Inspired by the present application, it is understood that the isotropic normalization may also use min(data(Y)) and max(data(Y)), or min(data(Z)) and max(data(Z)).

In 109, a first predicted vector corresponding to the z-axis of the local coordinate system is obtained using the trained deep learning artificial neural network based on the third digital data set.

In one embodiment, the first predicted vector may be predicted using Multi-Layer Perceptron (abbreviated as MLP) based on the third digital data set.

Figure 2:
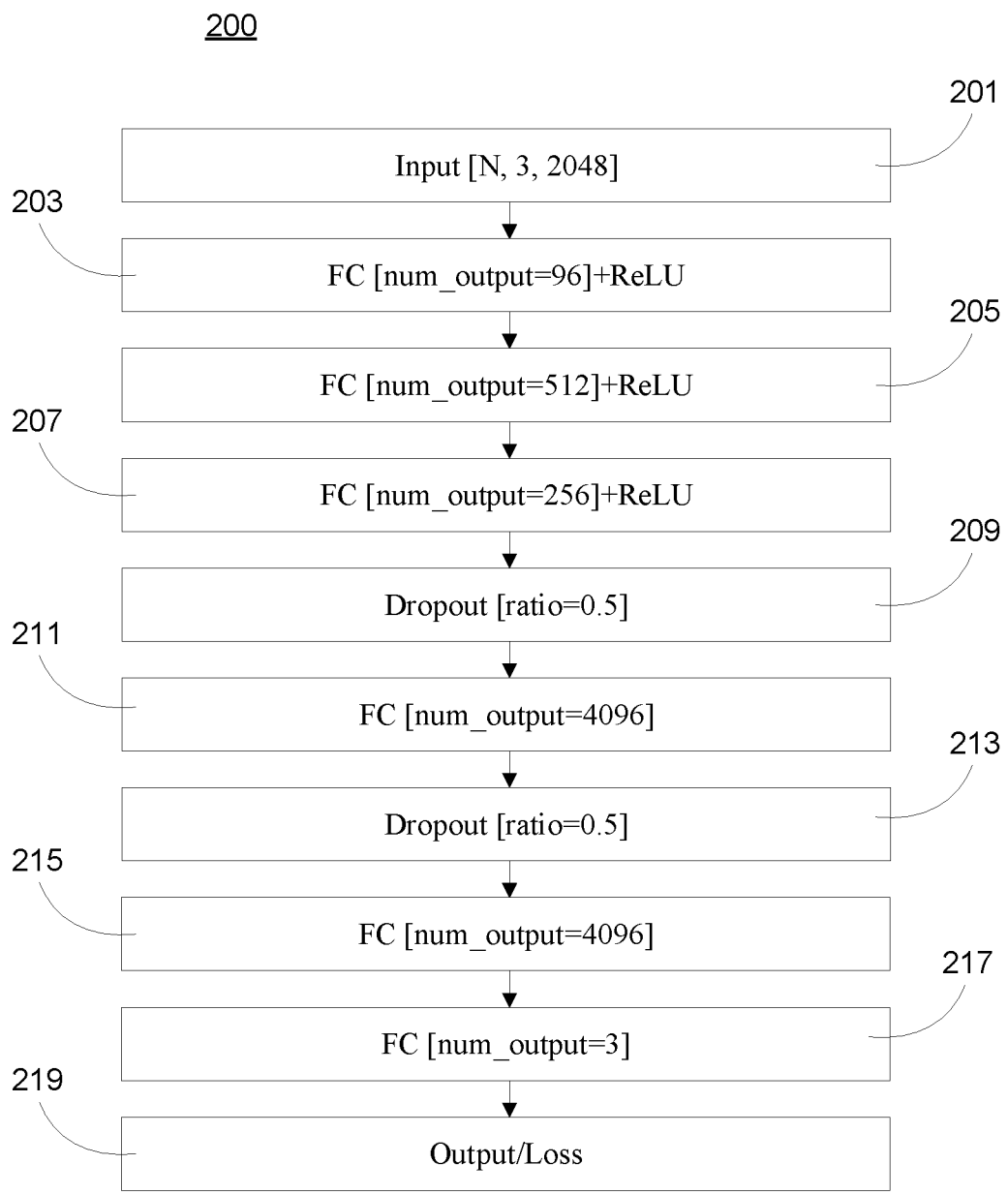
FIG. 2 schematically illustrates a structure of a multi-layer perceptron artificial neural network according to an embodiment of the present application.

Referring to FIG. 2, it schematically illustrates structure of a multi-layer perceptron artificial neural network 200 according to an embodiment of the present application.

In one embodiment, the multi-layer perceptron 200 comprises an input layer 201, six fully-connected layers 203, 205, 207, 211, 215 and 217, two Dropout layers 209 and 213, and an output layer 219.

The fully-connected layers 203, 205 and 207 comprise a ReLU activation function to achieve non-linearity, avoid gradient diffusion, and provide inclusiveness for the depth and breadth of the model. On the basis of retaining all input information, the fully-connected layers can improve fitting capability of the model through linear and nonlinear changes, and extract useful features.

The Dropout layers 209 and 213 can enhance generalization of the model and reduce the risk of overfitting.

[Training of the Multi-Layer Perceptron]

In one embodiment, the multi-layer perceptron may be trained using tooth 3D digital models with manually set local coordinate systems.

In one embodiment, one multi-layer perceptron artificial neural network may be established and trained for each different tooth, to improve prediction accuracy.

In one embodiment, in the training, the label item (namely, the learning direction of the artificial neural network) may be set as z-axis of local coordinate system. It is understood that the label item may also be set as y-axis of local coordinate system.

The output layer 219 comprises a EuclideanLoss cost function representing a root mean square error of a predicted result and a labeled result to thereby train parameters in layers of the MLP by Back Propagation (abbreviated as BP). The mathematical expression of the EuclideanLoss cost function may be written as:

$$\frac{1}{2N} \sum_{i=1}^{N} \|\text{label}_i - \text{prediction}_i\|_2^2$$

where N stands for the amount of data used in the training (namely, the number of 3D digital models of this type of teeth with manually set local coordinate systems used in the training), $\text{label}_i$ stands for the label item of the $i^{th}$ training data, and $\text{prediction}_i$ stands for an item predicted by the artificial neural network based on the $i^{th}$ training data.

The BP algorithm is a learning algorithm suitable for multi-layer neural networks under a supervised condition. It is established on the basis of a gradient descent method. The BP algorithm mainly comprises two sections (excitation propagation and weight updating) which repeatedly and cyclically iterate until the response of the network to the input reaches a predetermined target range. The learning process of the BP algorithm includes a forward propagation process and a back propagation process. In the forward propagation process, the input information is processed layer by layer through an input layer and then a hidden layer and transferred to an output layer. If a desired output value can not be obtained at the output layer, the cost function is taken as a objective function, the process turns to the back propagation, partial derivatives of the objective function with respect to weights of neurons are calculated layer by layer, to constitute a gradient of the objective function with respect to weight vectors, which forms the basis for modifying the weights. The learning of the network is completed during modification of the weights. When the error reaches the desired value, the learning of the network ends.

The first predicted vector output by the MLP may be three components along the X-axis, Y-axis and Z-axis of the world coordinate system. When the label item is the z-axis of the local coordinate system, the first predicted vector is the z-axis of the local coordinate system predicted by the MLP.

In one embodiment, the training process may be implemented using python in conjunction with caffe under the Ubuntu system. The training parameters and their values may be as follows:

max_iter: 40000
base_lr: 0.001 (or 0.01)
Lr_policy: step
Stepsize=20000 (or 40000)
Gamma: 0.1
Momentum: 0.9
Momentum2: 0.99
Weight_decay=0.005
Solver: SGDSolver
Weight_filler: Xavier Wherein the training rate base_lr and stepsize may be adjusted according to training feedbacks to obtain a better model.

In 111, the x-axis of the local coordinate system is determined using a normal-based principal component analysis algorithm, based on the second digital data set.

Referring to "Efficient 3D Shape Matching and Retrieval Using a Concrete Radialized Spherical Projection Representation" by Papadakis P, Pratikakis I, Perantonis S et al. published on Pattern Recognition, 2007, 40(9):2437-2452, it discloses a Normals Principal Component Analysis (abbreviated as NPCA) algorithm of 3D data.

The NPCA algorithm is insensitive to transformations such as points permutation, translation and rotation etc., and can very well describe a representation of a piece of facet data in a 3D coordinate system so that a lot of troubles on matching are avoided.

After a large number of experiments, the Inventors of the present application discovered that a certain feature vector obtained by analyzing data of a tooth using the NPCA algorithm highly matches the direction of the x-axis of the local coordinate system, and an angle between the two is less than one degree in about 99% cases. Therefore, the feature vector that meets the spatial conditions of the x-axis of the local coordinate system may be selected from three feature vectors obtained by processing the second digital data set using the NPCA algorithm, and the selected feature vector may be taken as the x-axis of the local coordinate system after it is given a correct sign.

Detailed description will be given to the process of determining the x-axis of the local coordinate system using the NPCA algorithm, wherein the coordinate axes of the world coordinate system are represented with X, Y and Z, and the coordinate axes of the local coordinate system are represented with x, y and z.

In one embodiment, the x-axis of the local coordinate system may be directly determined using the NPCA algorithm.

[Directly Determine the x-Axis of the Local Coordinate System Using the NPCA]

First, a normal vector $n_i$ and a surface area $E_i$ of each triangular facet are calculated.

Then, a covariance matrix may be calculated according to the following Equation (7):

$$C = \frac{1}{E}\sum_{i=1}^{N} E_i \cdot n_i \cdot n_i^T \qquad \text{Equation (7)}$$

where E stands for a sum of the surface areas of all triangular facets.

Then, three feature vectors x', y' and z' are calculated based on the calculated covariance matrix, which respectively correspond to the x-axis, y-axis and z-axis of the local coordinate system. x' is taken as the x-axis of the local coordinate system after it is given a correct sign.

At this time point, which one of the calculated three feature vectors corresponds to the x-axis of the local coordinate system cannot be determined yet. In one embodiment, it may be determined by the following method.

First, one feature vector which has a minimum angle with respect to the straight line where the Z-axis of the world coordinate system lies may be selected as the vector z' that corresponds to the z-axis of the local coordinate system. For teeth in the first or second quadrant, the angle between the feature vector and the —Z-axis vector is calculated; for the teeth in the third or fourth quadrant, the angle between feature vector and Z-axis vector is calculated.

Figure 3:
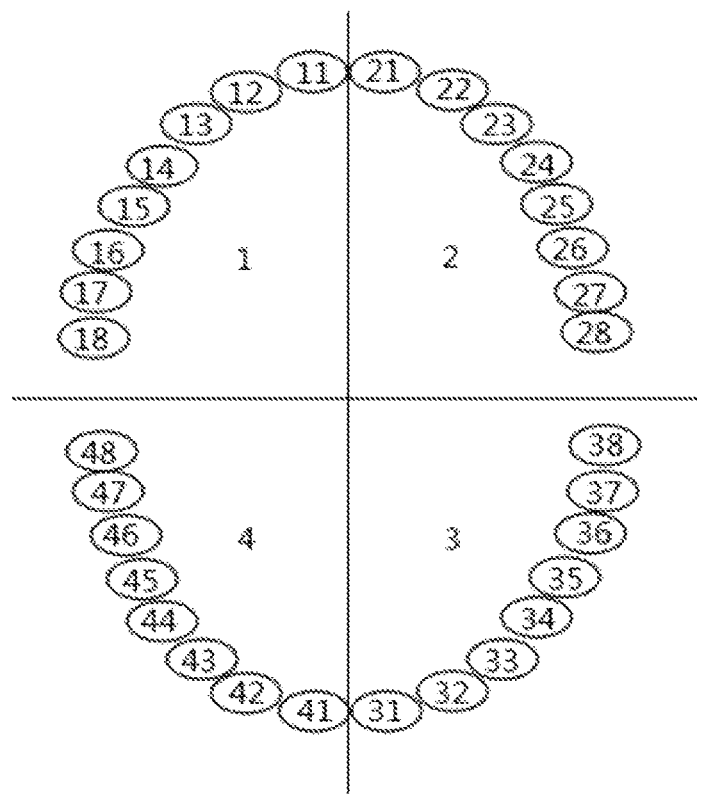
FIG. 3 schematically illustrates quadrant distribution of teeth.

Referring to FIG. 3, it schematically illustrates quadrant distribution of teeth.

The figure is a projection of teeth on the upper and lower jaws from back to front. The teeth in the first quadrant 1 and second quadrant 2 are teeth on the upper jaw, and teeth in the third quadrant 3 and fourth quadrant 4 are teeth on the lower jaw. The first digit in the serial number of each tooth is the tooth' quadrant number, and the second digit is tooth number. For example, the serial number of tooth No. 1 on the left of the upper jaw is 11, and so on so forth.

Then, one of the remaining two feature vectors is selected as x', and it is given a corresponding sign and taken as the x-axis of the local coordinate system. In one embodiment, which one of the remaining two feature vectors is x' may be determined by the following method.

In one embodiment, x', y' and z' may be used to establish a pseudo-coordinate system $x_1y_1z_1$. When direction changes are considered, there are four cases complying with the right-hand rule. The four cases are [x',y'] (the first vector in the remaining two feature vectors is taken as $x_1$ and the second vector is taken as $y_1$), [y',−x'] (the first vector in the remaining two feature vectors is taken as $y_1$ and the second vector is taken as $−x_1$), [−x',−y'] (the first vector in the remaining two feature vectors is taken as $−x_1$ and the second vector is taken as $−y_1$), and [−y',x'] (the first vector in the remaining two feature vectors is taken as $−y_1$ and the second vector is taken as $x_1$). For teeth Nos. 1-6, it may be processed according to the following rules based on positional relationship with the X-axis and Y-axis of the world coordinate system and shape differences between the teeth.

Rule 1: it may be specified that the component of x' on the X-axis of the world coordinate system is less than zero for the teeth in the first and fourth quadrants; it may be specified that the component of x' on the X-axis of the world coordinate system is larger than zero for the teeth in the second and third quadrants.

Rule 2: for the teeth in the first and second quadrants, it may be specified that the component of x' on the Y-axis of the world coordinate system is less than zero, and the component of y' on the X-axis of the world coordinate system is less than zero; for the teeth in the third and fourth quadrants, it may be specified that the component of x' on the Y-axis of the world coordinate system is less than zero, and the component of y' on the X-axis of the world coordinate system is larger than zero.

Rule 3: for the teeth in the first and fourth quadrants, it may be specified that when the component of x' on the X-axis of the world coordinate system is less than zero, the component of x' on the Y-axis of the world coordinate system is less than about −sin(pi/6), wherein the value is an empirical value obtained by the Inventors of the present application based on a large number of experiments; and it may be specified that when the component of x' on the X-axis of the world coordinate system is greater than zero, the component of x' on the Y-axis of the world coordinate system is less than about −sin(pi/3), wherein the value is an empirical value obtained by the Inventors of the present application based on a large number of experimentation. For the teeth in the second and third quadrants, it may be specified that when the component of x' on the X-axis of the world coordinate system is less than zero, the component of x' on the Y-axis of the world coordinate system is less than about −sin(pi/3); when the component of x' on the X-axis of the world coordinate system is greater than zero, the component of x' on the Y-axis of the world coordinate system is less than about −sin(pi/6).

Due to the peculiarity in geometry, for teeth Nos. 1-3, a midpoint between a maximum value and a minimum value in the z' direction may be taken as a dividing point, and an upper portion of the tooth crown is retained. Then, the NPCA is performed again for the upper portion of the tooth crown. In this case, it is great probability that the vector of the first principle component is substantially parallel to the straight line where the x-axis of the local coordinate system lies. Therefore, among the feature vectors of the NPCA of the entire tooth crown, the one having the minimum angle with respect to the vector of the first principle component of the NPCA of the upper portion tooth crown may be taken as x'. As a result, the above four cases may be simplified into two cases. Then, the direction of the x-axis of the local coordinate system may be determined according to rules 1 and 2.

For central incisors, x' and y' may be distinguished from each other based on the absolute values of the components along the X-axis of the world coordinate system, the feature vector with a larger absolute value is x', and the feature vector with a smaller absolute value is y'. This method may replace rule 2.

For teeth Nos. 4-6, after determination is made based on rule 3, there might be multiple cases that meet requirements, for example, [x', y'] and [y', −x'].

Medical rules provide that the x-axis of the local coordinate system should be parallel to the central groove. Further determination may be made based on the following rule.

10 sets of intersection lines at different x values between 10 sets of planes perpendicular to the x-axis of the local coordinate system and the tooth model may be obtained. In the two cases (namely, [x', y'] and [y', −x']), intersection line sets A and B are obtained, respectively. If there are more concave intersection lines in the intersection line set A, [x', y'] is more suitable; if there are more concave intersection lines in the intersection line set B, [y', −x'] is more suitable. To determine whether an intersection line is concave, intersection points between straight lines that z=a (a includes 10 values evenly spaced in the z value range of the curve) and an intersection line may be obtained. If the number of intersection points between one of the straight lines and the intersection line is larger than 2, it is determined that the curve is concave. The x-axis of the local coordinate system may be determined based on the numbers of concave intersection lines of the intersection line sets A and B.

For tooth No. 7, determination may be made according to the following rule 4. For the teeth in the first and third quadrants, the component of y' along the Y-axis of the world coordinate system shall be greater than −sqrt(3)/2, wherein the value is an empirical value obtained by the Inventors of the present application based on a large number of experiments; for the teeth in the second and fourth quadrants, the component of y' along the Y-axis of the world coordinate system shall be smaller than sqrt(3)/2.

If there are more than one case that satisfies the rules after determination is made according to rule 4 and rule 2, a combination with a minimum angle between the y-axis of the local coordinate system and the X-axis of the world coordinate system may be selected.

If the one to one correspondence still cannot be determined based on the above, a random result may be output, which is the source of the 1% error.

In another embodiment, the x-axis of the local coordinate system may also be determined using a combination of NPCA and MLP.

[Determine the x-Axis of the Local Coordinate System Using a Combination of NPCA and MLP]

In one embodiment, 28 MLP networks, each of which corresponds to one tooth, may be established and trained for the x-axis of the local coordinate system according to the above method.

Then, the third digital data set is input into the corresponding MLP network to obtain a second predicted vector, in other words, the MLP network predicts the x-axis of the local coordinate system based on the third digital data set.

Then, the second digital data set is processed using the NPCA to obtain three feature vectors x', y', z' corresponding to the x-axis, y-axis, z-axis of the local coordinate system, respectively. However, at this time point, the one to one correspondence between the three feature vectors and the x-axis, y-axis, z-axis of the local coordinate system still cannot be determined.

For teeth in different quadrants, one of the three feature vectors, which has a minimum angle with respect to the straight line where the Z-axis of the world coordinate system lies, is selected as z'.

The second predicted vector is compared with the straight lines where the remaining two feature vectors lie, and the feature vector having the minimum angle with respect to the second predicted vector is selected, given a correct sign and taken as the x-axis of the local coordinate system. For example, when the angle between the selected feature vector and the second predicted vector is less than 90 degrees, the selected feature vector is given the sign "+", which means its direction is not changed; when the angle between the selected feature vector and the second predicted vector is greater than 90 degrees, the selected feature vector is given the sign "−", which means its direction is reversed.

In 113, the y-axis and z-axis of the local coordinate system are determined based on the determined x-axis of the local coordinate system and the first predicted vector.

In one embodiment, the cross product between the determined x-axis of the local coordinate system and the first predicted vector may be calculated and taken as the y-axis of the local coordinate system. Then, the cross product between the determined x-axis and y-axis of the local coordinate system may be calculated and taken as the z-axis of the modified local coordinate system.

In one embodiment, the origin of the local coordinate system may be the center of the mesh boundary. The setting of the local coordinate system is now completed.

Figure 4:
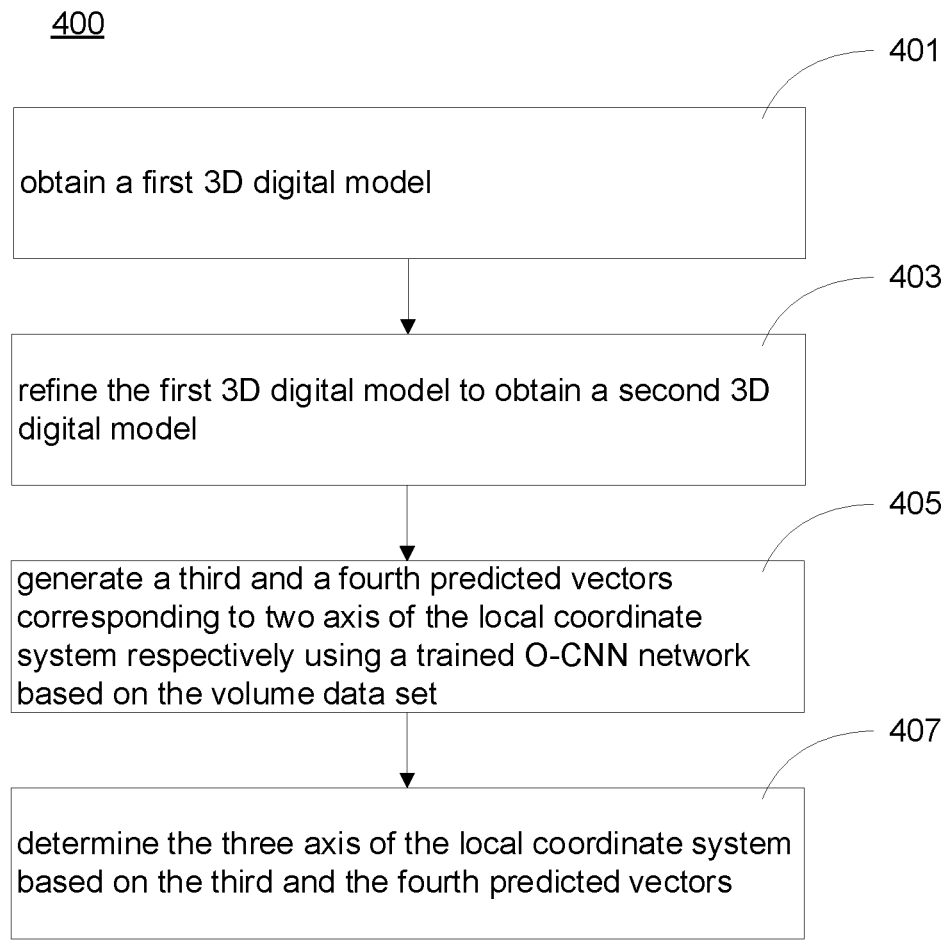
FIG. 4 schematically illustrates a flow chart of a computer-implemented method for setting a local coordinate system of a tooth 3D digital model according to an embodiment of the present application.

Referring to FIG. 4, it schematically illustrates a flow chart of a computer-implemented method 400 for setting a local coordinate system of a tooth 3D digital model according to an embodiment of the present application.

The computer-implemented method 400 for setting the local coordinate system of the tooth 3D digital model uses Octree-Based Convolutional Neural Networks (abbreviated as O-CNN).

In 401, a first 3D digital model is obtained.

The first 3D digital model is in the world coordinate system and represents a first tooth, in other words, coordinate values of its vertices are coordinate values in the world coordinate system.

In 403, the first 3D digital model is refined to obtain a second 3D digital model.

In one embodiment, to add more information to subsequently-voxelized data, the first 3D model may be up-sampled for refinement purpose to obtain the second 3D digital model. Specific operations are as follows:

First, midpoints $a_i$, $b_i$, $c_i$ of three sides of triangular facet $f_i$ are calculated.

Then, $a_i$ is connected with $b_i$, $a_i$ is connected with $c_i$, and $b_i$ is connected with $c_i$. At this time point, the original triangular facet $f_i$ is divided into four smaller triangular facets.

After the division of all triangular facets is completed, the above operations may be iterated until the empirical requirement is satisfied. In one embodiment, up-sampling may be performed four times for the first 3D digital model to obtain the second 3D digital model.

In 405, octree voxelization of the second 3D digital model is performed to obtain a volume data set.

In one embodiment, the second 3D digital model may be placed in a unit bounding box whose length, width and height are all equal to 1, then the unit bounding box may be recursively divided into eight sub-bounding boxes in a breadth-first order, and recursion may be repeated until a preset octree depth d is reached.

In one embodiment, some information such as shuffle key and O-label needed in the O-CNN transformation may be collected after the voxelization.

The shuffle key defines a relative position of a current child node under a parent node and it serves the convolution calculation. The O-label defines which node is the parent node of the current child node, and which non-empty child node under the parent node the current child node is. This process serves the pooling operation.

In 407, a third predicted vector and a fourth predicted vector corresponding to two of the coordinate axes of the local coordinate system are obtained using the trained O-CNN network, based on the volume data set.

In one embodiment, in the training of the O-CNN networks, three O-CNN networks may be established and trained for the three coordinate axes of the local coordinate system, respectively, and two O-CNN networks (corresponding to two of the coordinate axes of the local coordinate system, respectively) with the best prediction accuracy are selected according to the results in the training, to set the local coordinate system.

[Training of the O-CNN Networks]

In the training of the O-CNN networks, in order to improve the generalization capability of the O-CNN networks, the refined 3D digital models for training may be rotated about the three axes of the local coordinate system by [−45,45] degrees with a step of 15 degrees, and the data is therefore augmented $7^3$ times.

Referring to the paper "O-CNN: Octree-Based Convolutional Neural Networks for 3D Shape Analysis" by Wang P S, Liu Y, Guo Y X et al. published on Acm Transactions on Graphics, 2017, 36(4):72, it discloses a convolutional neural network with voxelized 3D data as input, which provides a very good solution for classification and segmentation of 3D models. For the prediction of the coordinate axes of the local coordinate system, the classification layer of the O-CNN may be replaced with a regression layer having Euclidean-Loss as the cost function.

Figure 5:
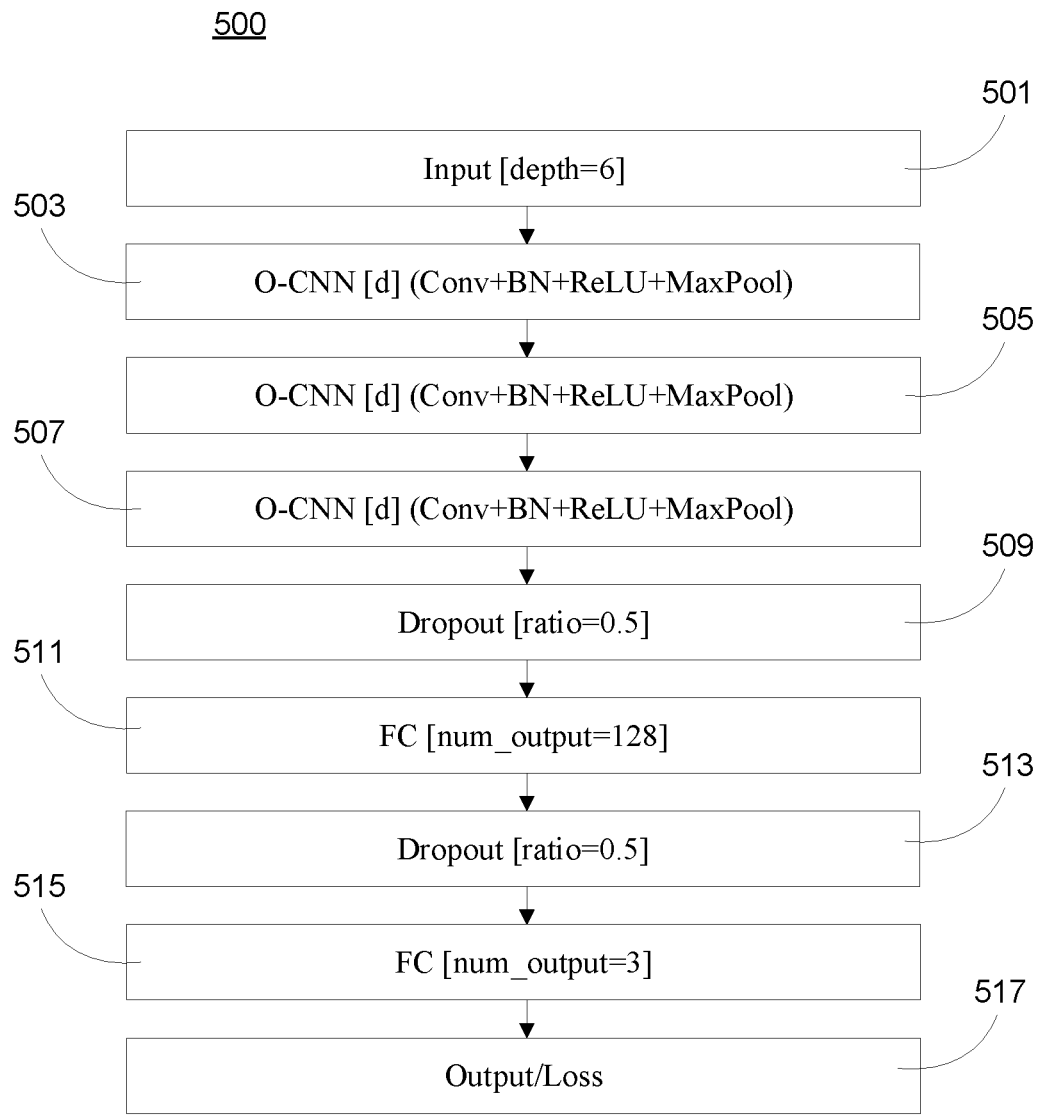
FIG. 5 schematically illustrates a structure of an O-CNN network according to an embodiment of the present application.

Referring to FIG. 5, it schematically illustrates the structure of the O-CNN network 500 according to an embodiment of the present application.

The O-CNN network 500 comprises an input layer 501, O-CNN[d] 503, 505 and 507, Dropout layers 509 and 513, fully-connected layers 511 and 515, and an output layer 517.

Each of the O-CNN[d] 503, 505 and 507 comprises a convolutional layer, a batch normalization layer, an activation function ReLU and a pooling layer. The convolutional layer calculates local features by convoluting data in a small area. The pooling layer partially achieves rotation and translation invariance by up-sampling. The batch normalization layer, to a certain degree, solves the non-uniform distribution of output data of each layer, and has advantages such as being able to use a higher learning rate, avoid overfitting and reasonably avoid gradient saturation.

In one embodiment, the input data value is an average normal of all vertices within the bounding box in which each leaf node lies. If the leaf node is empty, the normal is set to 0.

In 409, the three coordinate axes of the local coordinate system are determined based on the third predicted vector and fourth predicted vector.

In one embodiment, it may be determined which of the third predicted vector and the fourth predicted vector shall be taken as the first coordinate axis of the local coordinate system based on prediction bias of the O-CNN network. Then, the cross product of the third predicted vector and the fourth predicted vector is taken as the second coordinate axis of the local coordinate system. In the end, the cross product of the first coordinate axis and second coordinate axis is taken as the third coordinate axis of the local coordinate system.

For example, if the third predicted vector corresponds to the x-axis of the local coordinate system and the fourth predicted vector corresponds to the z-axis of the local coordinate system, and if the O-CNN network's prediction of the x-axis of the local coordinate system is more accurate, the third predicted vector is taken as the x-axis of the local coordinate system. Then, the cross product of the third predicted vector and the fourth predicted vector is taken as the y-axis of the local coordinate system. In the end, the cross product of the x-axis and the y-axis is taken as the z-axis of the local coordinate system.

Inspired by the present application, it is understood that in addition to the above deep learning artificial neural networks, other suitable artificial neural networks may also be used to set the coordinate axes of the local coordinate system, for example, Convolutional Neural Networks (CNN), Recurrent Neural Networks (RNN), Reinforcement Learning (RL) and Generative Adversarial Networks (GANs).

While various aspects and embodiments have been disclosed herein, other aspects and embodiments will be apparent to those skilled in the art, inspired by the present application. The various aspects and embodiments disclosed herein are for illustration only and are not intended to be limiting, and the scope and spirit of the present application shall be defined by the following claims.

Likewise, the various diagrams may depict exemplary architectures or other configurations of the disclosed methods and systems, which are helpful for understanding the features and functions that can be included in the disclosed methods and systems. The claimed invention is not restricted to the illustrated exemplary architectures or configurations, and desired features can be achieved using a variety of alternative architectures and configurations. Additionally, with regard to flow diagrams, functional descriptions and method claims, the order in which the blocks are presented herein shall not mandate that various embodiments of the functions shall be implemented in the same order unless otherwise the context specifies.

Unless otherwise specifically specified, terms and phrases used herein are generally intended as "open" terms instead of limiting. In some embodiments, use of phrases such as "one or more", "at least" and "but not limited to" should not be construed to imply that the parts of the present application that do not use similar phrases intend to be limiting.

We claim:

1. A computer-implemented method for setting a local coordinate system for a tooth 3D digital model, comprising:
    obtaining a first 3D digital model representing a first tooth, wherein the first 3D digital model is based on a world coordinate system;
    obtaining a first predicted vector using a first artificial neural network based on the first 3D digital model, wherein the first artificial neural network is a trained deep learning artificial neural network and is configured to predict an x-axis of a local coordinate system of the first 3D digital model,
        wherein the first predicted vector corresponds to an x-axis of the local coordinate system,
            wherein the x-axis is substantially parallel to a central groove of the first tooth;
    generating three feature vectors using a principal component analysis method based on the first 3D digital model;
    selecting one from the three feature vectors, which has a minimum angle with respect to a straight line where the first predicted vector lies, giving the selected feature vector a correct sign according to the first predicted vector, and designating the selected feature vector as the x-axis of the local coordinate system;
    obtaining the second predicted vector using a second artificial neural network based on the first 3D digital model,
        wherein the second predicted vector corresponds to a first coordinate axis of the local coordinate system,
            wherein the first coordinate axis is first one of a y-axis or a z-axis of the local coordinate system,
            wherein a second one of the y-axis or the z-axis of the local coordinate system is a second coordinate axis of the local coordinate system;
    determining the first coordinate axis based on the determined x-axis and the second predicted vector; and
    determining the second coordinate axis based on the determined x-axis and the first coordinate axis.

2. The computer-implemented method of claim 1, wherein the first artificial neural network is a multi-layer perceptron.

3. The computer-implemented method of claim 2, wherein an output layer of the first artificial neural network comprises an Euclidean Loss cost function for training parameters of various layers by back propagation.

4. The computer-implemented method of claim 1, wherein the principal component analysis method is a Normals Principal Component Analysis method.

5. The computer-implemented method of claim 1, wherein the first coordinate axis of the local coordinate system is the z-axis.

6. The computer-implemented method of claim 1 further comprising: simplifying the first 3D digital model such that a number of its vertices is equal to a predetermined number N, to obtain a first digital data set, and obtaining the first predicted vector using the first artificial neural network based on the first digital data set, wherein N is a natural number.

7. The computer-implemented method of claim 6 further comprising: centralizing the simplified data set to obtain a second digital data set, obtaining the first predicted vector using the first artificial neural network based on the second digital data set, and determining the x-axis of the local coordinate system using the principal component analysis method based on the second digital data set.

8. The computer-implemented method of claim 7 further comprising: normalizing the second digital data set to obtain a third digital data set, and obtaining the first predicted vector using the first artificial neural network based on the third digital data set.

9. The computer-implemented method of claim 1 further comprising: selecting the first artificial neural network from a plurality of artificial neural networks according to a type of the first tooth, where the plurality of artificial neural networks are trained deep learning artificial neural networks for setting local coordinate systems for different types of teeth respectively.

10. The computer-implemented method of claim 1, wherein the first artificial neural network is one of: a Multi-layer Perceptron, an Octree-Based Convolutional Neural Network, a Convolutional Neural Network, a Recurrent Neural Network, Reinforcement Learning and a Generative Adversarial Network.

11. The computer-implemented method of claim 1, wherein the first artificial neural network is trained with a plurality of tooth 3D digital models each having a manually-set local coordinate system, wherein each of the plurality of tooth 3D digital models represents a tooth which is a same type as the first tooth.

* * * * *